(12) United States Patent
Yaroshenko et al.

(10) Patent No.: US 12,394,055 B2
(45) Date of Patent: Aug. 19, 2025

(54) SPECTRAL DARK-FIELD IMAGING

(71) Applicant: KONINKLIJKE PHILIPS N.V., Eindhoven (NL)

(72) Inventors: Andriy Yaroshenko, Garching (DE); Thomas Koehler, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 137 days.

(21) Appl. No.: 18/008,651

(22) PCT Filed: Jun. 3, 2021

(86) PCT No.: PCT/EP2021/064895
§ 371 (c)(1),
(2) Date: Dec. 6, 2022

(87) PCT Pub. No.: WO2021/249855
PCT Pub. Date: Dec. 16, 2021

(65) Prior Publication Data
US 2023/0222658 A1   Jul. 13, 2023

(30) Foreign Application Priority Data
Jun. 8, 2020   (EP) .................................... 20178684

(51) Int. Cl.
*A61B 6/00*   (2024.01)
*A61B 6/40*   (2024.01)
(Continued)

(52) U.S. Cl.
CPC ............ *G06T 7/0014* (2013.01); *A61B 6/405* (2013.01); *A61B 6/4241* (2013.01); *A61B 6/482* (2013.01);
(Continued)

(58) Field of Classification Search
CPC ......... G06T 7/0014; G06T 7/11; G06T 7/174; G06T 2207/10116; G06T 2207/20221;
(Continued)

(56) References Cited

U.S. PATENT DOCUMENTS 10,506,993 B2   12/2019   Martens
10,631,808 B2 *   4/2020   Proksa ................. A61B 6/5217
(Continued)

FOREIGN PATENT DOCUMENTS

EP   3391819 A1   10/2018
EP   3496109 A1   12/2019
(Continued)

OTHER PUBLICATIONS

PCT International Search Report, International application No. PCT/EP2021/064895, Aug. 13, 2021.

*Primary Examiner* — David P Porta
*Assistant Examiner* — Mamadou Faye
(74) *Attorney, Agent, or Firm* — Larry Liberchuk

(57) ABSTRACT

This invention relates to an image processing device (1) comprising an input (2) for receiving image data representative of a region of interest in the body of a patient from a medical X-ray imaging apparatus (100). The image data comprises a first dark-field image obtained for a first X-ray spectrum and a second dark-field image obtained for a second, different. X-ray spectrum. A combination unit (3) provides a combination image that is representative of a medical condition map. e.g. a lung condition map, by combining the first dark-field image and the second dark-field image.

11 Claims, 2 Drawing Sheets

(51) Int. Cl.
*A61B 6/42* (2024.01)
*G06T 7/00* (2017.01)
*G06T 7/11* (2017.01)
*G06T 7/174* (2017.01)
*G06V 10/80* (2022.01)

(52) U.S. Cl.
CPC ................ *G06T 7/11* (2017.01); *G06T 7/174* (2017.01); *G06V 10/809* (2022.01); *G06T 2207/10116* (2013.01); *G06T 2207/20221* (2013.01); *G06T 2207/30061* (2013.01)

(58) Field of Classification Search
CPC .......... G06T 2207/30061; A61B 6/405; A61B 6/4241; A61B 6/482; A61B 6/50; A61B 6/5217; A61B 6/484; A61B 6/483; G06V 10/809
See application file for complete search history.

(56) References Cited

U.S. PATENT DOCUMENTS

| | | | |
|---|---|---|---|
| 11,116,465 B2 | 9/2021 | Proksa | |
| 11,529,112 B2 | 12/2022 | Bartels | |
| 2015/0139383 A1 | 5/2015 | Proksa | |
| 2016/0374635 A1* | 12/2016 | Ning | G01N 23/20091 378/5 |
| 2017/0316588 A1* | 11/2017 | Homann | G06T 11/008 |
| 2017/0345191 A1* | 11/2017 | Koehler | G06T 5/70 |
| 2018/0228455 A1 | 8/2018 | Koehler | |
| 2018/0271465 A1* | 9/2018 | Proksa | G16H 50/30 |
| 2018/0360313 A1* | 12/2018 | Zhang | G06T 7/337 |

FOREIGN PATENT DOCUMENTS

| | | | |
|---|---|---|---|
| JP | 2018192909 A | 12/2018 | |
| WO | WO2017211625 A1 | 12/2017 | |
| WO | WO-2018114553 A1 * | 6/2018 | ............. A61B 6/484 |

* cited by examiner

SPECTRAL DARK-FIELD IMAGING

FIELD OF THE INVENTION

The present invention relates to the field of dark-field imaging, e.g. in medical diagnostic applications. Specifically, the invention relates to an image processing device, a method for image processing, an imaging system and a related computer program product, for medical diagnostic imaging, e.g. to aid in the detection and diagnosis of different pulmonary conditions.

BACKGROUND OF THE INVENTION

X-ray dark-field imaging, as known in the art, is a useful and remarkably versatile ionizing radiation imaging modality, e.g. for medical diagnostic applications. It is specifically advantageous that information can be gleaned from X-ray dark-field image data about structures at a scale below the spatial resolution limits of the imaging system.

It is known that this imaging modality can be used to achieve a highly sensitive detection, for example in detection of pulmonary disorders. Considering the representative example of lung imaging, it is noted that the alveoli of the lungs, which are responsible for the gas exchange between the blood and the inhaled air, are particularly small and delicate structures. While these alveoli are difficult, or even impossible, to image directly (at least by non-invasive imaging), useful information about the alveoli, and potentially disorders thereof, can be conveyed by the ionizing radiation scattering properties of the alveoli for small-angle scattering. These small-angle scattering properties can be characterized by X-ray dark-field imaging, such that this modality is particularly useful for the accurate detection of pulmonary disorders. Unfortunately, the observed signal changes detected by X-ray dark-field imaging may lack specificity. For example, the type of a pulmonary disorder cannot be easily determined by solely relying on the dark-field signal. Thus, a need exists in the art to provide good means and methods that allow different pulmonary disorders to be disambiguated, while, preferably, concomitantly preserving the high detection sensitivity to pulmonary disorders of dark-field imaging, e.g. at a sensitivity that is at least comparable to prior-art dark-field imaging methods.

An x-ray dark-field radiography image, obtained by methods known in the art, enables a clinician to detect a deviation from the expected healthy state of the lung, but not to distinguish different kinds of pulmonary disorders from the dark-field image, since many of such disorders lead to quite similar changes, e.g. local reductions, of the x-ray dark-field signal. For example, emphysema may cause a significant increase of the size of the alveoli, while acute inflammation may lead to the affected alveoli filling up with fluids or cell matter. Nonetheless, both disorders present a similar decrease in the x-ray dark-field signal, such that additional data would typically be needed for a differential diagnosis and, hence, to allow a suitable therapy, treatment or disease management approach for the patient to be determined.

US 2018/271465 discloses a prior-art method in which X-ray dark-field imaging information is used in a lung examination of a patient. In this approach, a lung depth map is calculated from attenuation image data; after a lung segmentation and bone suppression algorithm has been applied. The X-ray dark-field image is then normalized using the spatially corresponding estimated lung thickness values to obtain a map that is indicative of a lung condition, e.g. Chronic Obstructive Pulmonary Disorder (COPD). While COPD is typically not visible on conventional X-ray attenuation images, the normalized dark-field image is particularly sensitive to such a condition that affects the alveoli microstructures.

While the present description focuses on pulmonary imaging as a representative example and application, it will be understood by the person skilled in the art that methods and devices in accordance with embodiments can be more broadly applied to different applications. For example, bone structure bears many similarities to the lung structure, in which the small-angle scattering behavior of lung alveoli can be considered analogous to scattering on bone trabeculae. Furthermore, the intricate structure of the human or animal body encompasses many structures with similar characteristics, to which the teachings of the present disclosure can be applied. Another example of microstructures that might present a comparable scattering behavior are the kidney nephrons.

SUMMARY OF THE INVENTION

It is an object of embodiments of the present invention to provide easy, effective, efficient and/or good means and/or methods for processing diagnostic images to allow disambiguation of different disorders and/or medical conditions, e.g. to assist in a differential diagnosis of pulmonary disorders.

It is an advantage of embodiments of the present invention that the high detection sensitivity to pulmonary or other disorders of dark-field imaging, as currently achievable in the art, can be advantageously combined with methods and/or devices in accordance with embodiments of the present invention to achieve a good detection specificity (and/or selectivity) for a plurality of different conditions or disorders, such as different pulmonary disorders, as well.

It is an advantage of embodiments of the present invention that methods and/or devices in accordance with embodiments can be easily adapted to work with readily available X-ray imaging devices and/or can be easily included in established medical imaging methodologies and/or workflows.

It is an advantage of embodiments of the present invention that multi-spectral, e.g. dual-energy, X-ray attenuation information can be used for image segmentation and/or bone suppression and/or pixel value normalization, while using (typically concomitantly acquired) multi-spectral X-ray dark-field information to detect and disambiguate different types of pulmonary disorders.

It is an advantage of embodiments of the present invention that a pulmonary condition associated with a state of normal or abnormal function of alveoli in the lungs can be detected and discerned from different, yet similar, such conditions.

It is an advantage of embodiments of the present invention that different bone conditions, such as osteoporosis and bone edema can be detected and discerned from one another.

It is an advantage of embodiments of the present invention that different conditions, which present a similar or nearly identical image in a conventional dark-field X-ray image acquired with a single peak photon energy (i.e. a single spectrum), or at least are difficult to distinguish in such image, can be more easily differentiated in accordance with embodiments of the present invention.

It is an advantage of embodiments of the present invention that information about normal or abnormal function of alveoli, and pulmonary disorders associated therewith, can be gleaned from images obtained by an imaging modality that can have (e.g. despite having) a spatial detection threshold, e.g. a spatial resolution, that is insufficient to image such alveoli individually or even to image the microstructure of such alveoli in detail.

A device, method, system and computer program product in accordance with embodiments of the present invention achieves the above objective.

In a first aspect, the present invention relates to an image processing device comprising an input for receiving image data representative of a region of interest in the body of a patient from a medical X-ray imaging apparatus. The image data comprises a first dark-field image obtained for a first X-ray spectrum and a second dark-field image obtained for a second X-ray spectrum, in which the first X-ray spectrum and the second X-ray spectrum are (substantially) different. The image processing device comprises a combination unit adapted for providing a combination image that is representative of a condition map by combining the first dark-field image and the second dark-field image. For example, the condition map may be a map of anatomical, physiological and/or disease conditions, e.g. which conditions may be (not necessarily) specific to the region of interest.

In an image processing device in accordance with embodiments of the present invention, the region of interest may be the thorax region, wherein the condition map may be a lung condition map.

In an image processing device in accordance with embodiments of the present invention, the region of interest may be a bone region, and the condition map may be a map of bone conditions, such as osteoporosis and bone edema.

In an image processing device in accordance with embodiments of the present invention, the combination unit may be adapted for constructing the combination image as a vector-valued image, in which components of the vector-valued image correspond to, or are calculated on the basis of, the first dark-field image and the second dark-field image.

In an image processing device in accordance with embodiments of the present invention, the combination unit may be adapted to determine, for pixel locations in the combination image, a dark-field signal as function of photon energy or as function of correlation length.

In an image processing device in accordance with embodiments of the present invention, the combination unit may be adapted to calculate a measure of deviation between the first dark-field image and the second dark-field image, wherein pixel values in the combination image correspond to said measure of deviation.

In an image processing device in accordance with embodiments of the present invention, the input may be adapted for receiving said image data, wherein said image data comprises at least three dark-field images obtained for a corresponding at least three different X-ray spectra.

An image processing device in accordance with embodiments of the present invention may comprise a controller for controlling the operation of the X-ray imaging apparatus, when connected thereto, such as to acquire said image data.

In an image processing device in accordance with embodiments of the present invention, the controller may be adapted for stepping through a plurality of phase steps by controlling a phase stepper mechanism of the X-ray imaging apparatus, acquiring image data from an image detector of the X-ray imaging apparatus for each of a plurality of phase steps, and for controlling an X-ray source of the X-ray imaging apparatus such as to switch between the first X-ray spectrum for at least one of the plurality of phase steps and the second X-ray spectrum for at least another of the plurality of phase steps.

An image processing device in accordance with embodiments of the present invention may comprise a segmenter for segmenting the first dark-field image, the second dark-field image, the combination image, and/or another image received via the input, to identify structures, such as lung structures, of interest.

An image processing device in accordance with embodiments of the present invention may comprise a classifier (i.e. a classification unit) for labelling each identified structure of interest with a classifier label that is selected by the classifier from a plurality of classifier labels based on the combination image, said plurality of classifier labels corresponding to different conditions, e.g. different pulmonary conditions.

In a second aspect, the present invention relates to an X-ray imaging system comprising an image processing device in accordance with embodiments of the first aspect of the present invention and an X-ray imaging apparatus configured to acquire a plurality of X-ray dark-field images of a region of interest (e.g. of the chest, or of a bone region, . . . ) of a patient for a corresponding plurality of X-ray spectra and to provide said X-ray dark-field images to the input of the image processing device.

In an imaging system in accordance with embodiments of the present invention, the X-ray imaging apparatus may comprise an X-ray source and an X-ray (e.g. image) detector.

In an image processing device in accordance with embodiments of the present invention, the X-ray detector may be an energy-resolving photon counting detector.

In an image processing device in accordance with embodiments of the present invention, the X-ray imaging apparatus may be a dual-energy imaging apparatus or a spectral imaging apparatus.

An image processing device in accordance with embodiments of the present invention may comprise a registration unit for spatially registering the plurality of X-ray dark-field images such as to compensate for motion of the patient between the acquisitions of the images.

In an image processing device in accordance with embodiments of the present invention, the X-ray imaging apparatus may comprise a grating interferometer arrangement for differential phase contrast and dark-field imaging.

In a third aspect, the present invention relates to a clinical workstation comprising an image processing device in accordance with embodiments of the first aspect of the present invention.

In a fourth aspect, the present invention relates to a method, e.g. a computer-implemented method, for processing image data. The method comprises obtaining image data representative of a region of interest in the body of a patient from a medical X-ray imaging apparatus. The image data comprises a first dark-field image obtained for a first X-ray spectrum and a second dark-field image obtained for a second X-ray spectrum, wherein said first X-ray spectrum and said second X-ray spectrum are substantially different. The method comprises providing a combination image that is representative of a condition map by combining the first dark-field image and the second dark-field image.

In a method in accordance with embodiments of the present invention, the region of interest may be a thorax region. The condition map may be a lung condition map.

In a fifth aspect, the present invention relates to a computer program product for performing a (e.g. computer-implemented) method in accordance with the fourth aspect of the present invention when executing the computer program product on a suitable processor.

In a sixth aspect, the present invention relates to a medical diagnostic image of a region of interest in the body (e.g. a chest region, a bone region, . . . ) of a patient, comprising a combination of a first dark-field image obtained for a first X-ray spectrum and a second dark-field image obtained for a second X-ray spectrum, wherein the first X-ray spectrum and the second X-ray spectrum are (sufficiently) different.

Where reference is made to the first spectrum and the second spectrum being substantially different, i.e. sufficiently different, it will be understood by the skilled person that this means that the first X-ray spectrum and the second X-ray spectrum differ enough to obtain complementary information from the images obtained for these different spectra. Thus, the spectra may differ by at least 1 kV, preferably by at least 5 kV, in the mean energy or in the peak energy (kVp) of the spectra, preferably by at least 10 kV, e.g. by at least 20 kV, or even by a larger difference, e.g. at least 50 kV. It is to be noted that spectra can still differ substantially, even for the same peak photon energy (kVp), e.g. by being filtered by different beam conditioning filters, i.e. a different selection of beam filtration.

It will also be understood that embodiments of the present invention may equally relate to image data being acquired and/or used that comprises a plurality of dark-field images obtained for respectively a first X-ray spectrum, a second X-ray spectrum, optionally a third X-ray spectrum, optionally a fourth X-ray spectrum, etc. In other words, the number of dark-field images obtained for different spectra can be extended to any number (greater than one), e.g. as a specific application may need or benefit from. The skilled person will understand that the number of spectra that are used may be selected on the basis of a trade-off between gaining accuracy and/or further discriminating information by combining a larger number of images and increasing complexity and costs, e.g. costs in terms of operating time, processing resources, energy consumption and/or evaluation time by a clinician.

The independent and dependent claims describe specific and preferred features of the invention. Features of the dependent claims can be combined with features of the independent claims and with features of other dependent claims as deemed appropriate, and not necessarily only as explicitly stated in the claims.

Figure 1:
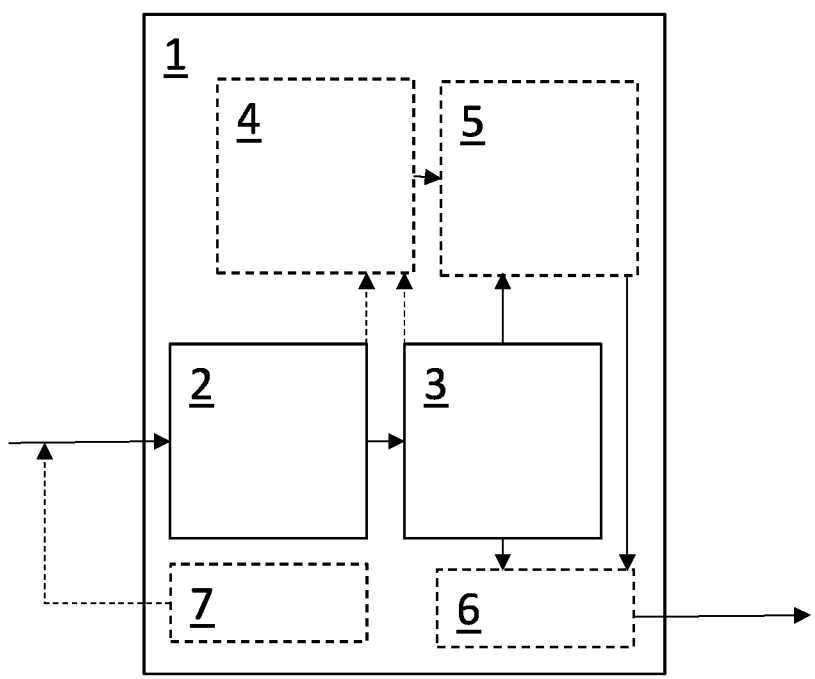
FIG. 1 schematically illustrates a device in accordance with embodiments of the present invention.

The drawings are schematic and not limiting. Elements in the drawings are not necessarily represented on scale. The present invention is not necessarily limited to the specific embodiments of the present invention as shown in the drawings.

DETAILED DESCRIPTION OF EMBODIMENTS

Notwithstanding the exemplary embodiments described hereinbelow, is the present invention only limited by the attached claims. The attached claims are hereby explicitly incorporated in this detailed description, in which each claim, and each combination of claims as allowed for by the dependency structure defined by the claims, forms a separate embodiment of the present invention.

The word "comprise," as used in the claims, is not limited to the features, elements or steps as described thereafter, and does not exclude additional features, elements or steps. This therefore specifies the presence of the mentioned features without excluding a further presence or addition of one or more features.

In this detailed description, various specific details are presented. Embodiments of the present invention can be carried out without these specific details. Furthermore, well-known features, elements and/or steps are not necessarily described in detail for the sake of clarity and conciseness of the present disclosure.

In a first aspect, the present invention relates to a medical image processing device. This medical image processing device may advantageously use dark-field image information acquired for two or more different x-ray spectra, e.g. using a dual-energy or spectral X-ray imaging system, to increase the specificity of x-ray dark-field imaging for diagnostic purposes in the evaluation of conditions afflicting a predetermined region of interest, e.g. the lung(s) or another organ or body structure. For example, different pulmonary disorders may affect the lung alveoli differently, and these different effects can be detected and discerned from each other after processing by a medical image processing device in accordance with embodiments of the present invention.

Referring to FIG. 1, an illustrative image processing device 1 in accordance with embodiments of the present invention is shown. The image processing device 1 may comprise a computer, e.g. specifically programmed for implementing the functionality of the device as described. Such computer may comprise inputs and outputs, e.g. communication interface(s) for receiving data and sending data, e.g. via a data carrier and/or communication network interface. Such inputs and outputs may also comprise user interface hardware, e.g. a human interaction device for receiving input from a human user (e.g. a keyboard, a mouse, a voice interpreter, a touch interface, a gyroscope or accelerometer, etc.), a monitor for presenting information to the user, a speaker, a printer for rendering information onto a physical carrier, such as paper, a three-dimensional printer for generating a three-dimensional physical model of data, and other such elements as known in the art.

The computer may comprise a general-purpose processor for carrying out instructions, e.g. a computer code, and a memory for storing such instructions. The computer may comprise a memory for storing data, e.g. for manipulating data in accordance with the instructions. The device is not necessarily limited to a general-purpose computer, but may also comprise an application specific integrated circuit (ASIC) and/or configurable processing hardware, e.g. a field-programmable gate array (FPGA). Furthermore, the device 1 may be comprised in a single processing device, e.g. a computer, but may also be distributed over a plurality of such devices that are operably connected to each other, e.g. such that the processing described herein is carried out by the joint action of a server and (a) client device(s), or of a parallel processing system, such as a computing cluster.

Figure 2:
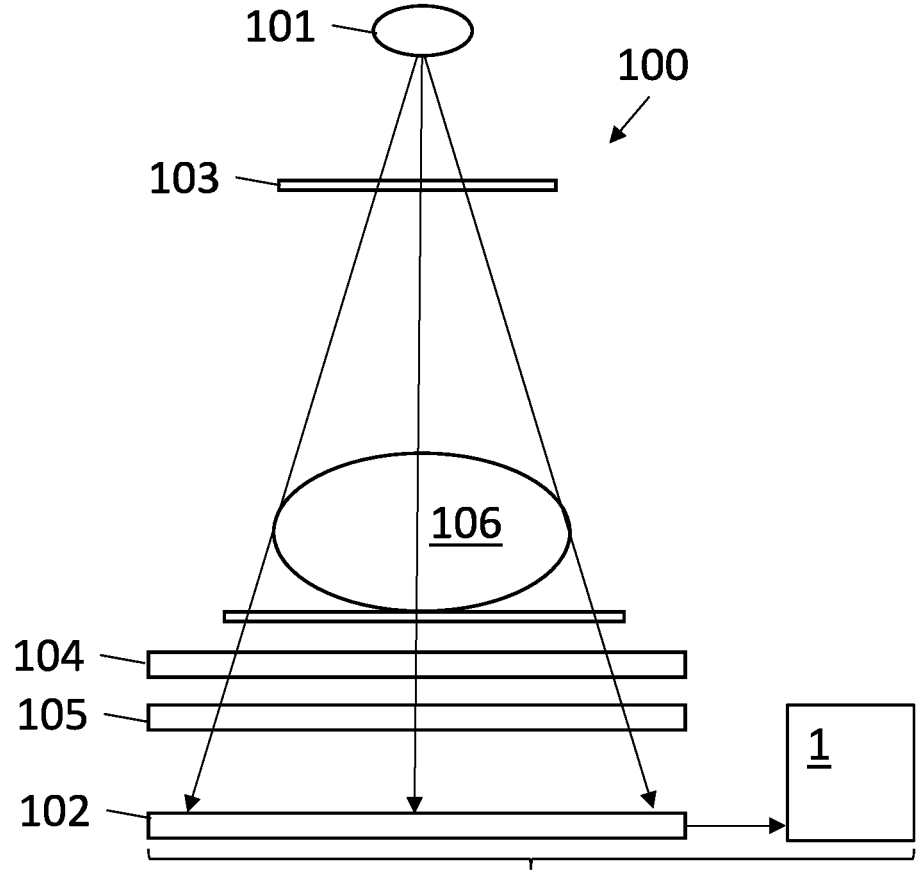
FIG. 2 shows a system in accordance with embodiments of the present invention.

In a second aspect, the present invention also relates to a medical imaging system. FIG. 2 schematically illustrates such a system 10 in accordance with embodiments of the present invention. The system 10 comprises an image processing device 1 in accordance with embodiments of the first aspect of the present invention. The system 10 also comprises an X-ray imaging apparatus 100, configured to supply image data to an input 2 of the image processing device 1. It will be understood that the 'input' can be a physical connection, e.g. using signal wiring, connectors and the like, but only requires an operational connection, e.g. could refer to a connection via a data communication network, a wireless connection, or even a connection via a removable data carrier that can be connected to the imaging apparatus 100 to receive and store image data and can be (e.g. subsequently) connected to the processing device 1 to provide access to the stored data. Furthermore, the image processing device 1 may be co-integrated with processing and/or control components of the imaging apparatus 100, e.g. as a software component configured to execute on a computing device, which may be used to execute other functions of the imaging apparatus as well. For example, the 'input' 2 may merely refer to a shared memory (volatile or non-volatile) via which one part of the imaging system makes the image data available to the processing device 1 (e.g. in the form of another part of the imaging system, possible only comprising software).

The X-ray imaging apparatus 100, e.g. an X-ray image acquisition device, may comprise an X-ray source and an X-ray detector. The X-ray imaging apparatus may be configured to acquire X-ray dark-field information of the chest of a patient at different representative energies, e.g. for different X-ray spectra. While most X-ray imaging systems have an adjustable photon energy setting, e.g. kVp, it is to be noted that the X-ray imaging apparatus may be specifically adapted for concomitantly acquiring the X-ray dark-field information for the different spectra, i.e. simultaneously or at least rapidly in succession (e.g. with a delay less than 10 seconds, preferably less than 1 second, even more preferred less than 100 ms, and even more preferred less than 10 ms). The X-ray imaging apparatus may also be adapted to concomitantly acquire X-ray attenuation information and/or X-ray phase contrast information. It is to be noted that the X-ray imaging apparatus may also be adapted to acquire the X-ray dark field image information at the different representative energies in succession at a relative low speed, e.g. with a delay of more than 10 seconds between the different spectral acquisitions. The X-ray imaging apparatus 100 or the device 1 may comprise a registration unit to compensate for motion of the patient between the acquisitions (i.e. to correct the first and/or second dark-field image such as to ensure a good alignment of corresponding image features in the different images). The latter may be particularly useful if the X-ray imaging apparatus is not specifically adapted for simultaneous acquisition of images for different spectra (e.g. energy ranges or bins) or for switching between spectra at a high switching speed.

The device 1 comprises an input 2 for receiving image data representative of a region of interest in the body of a patient, such as a patient's thorax region, e.g. a patient's chest or part thereof, from a medical X-ray imaging apparatus 100, in which the image data comprises a first dark-field image obtained for a first X-ray spectrum and a second dark-field image obtained for a second X-ray spectrum. The second X-ray spectrum substantially differs from the first X-ray spectrum. 'Image data' may refer to any type of information, e.g. typically digital data, that originates from the X-ray imaging apparatus and that is suitable for being used to construct a visual representation of the region of interest, e.g. of the patient's thorax region (or the imaged part thereof). In other words, this term should not be construed narrowly as only referring to a matrix of pixel data, but equally may be, for example, compressed, encrypted and/or encoded image data, in a processed format (e.g. segmented image data, annotated image data), in a raw format (e.g. data signals as directly recorded by an image sensor or detector), in a vector-valued format (e.g. a matrix comprising multiple values per pixel), and/or in a parametric representation, e.g. a parametric description of iso-intensity (iso-value) curves, segmented contours and/or surfaces in the image.

The first and second dark-field image may be obtained by collecting small-angle X-ray scattering information for different source spectra, e.g. generated in accordance with different peak energies and/or material filtration parameters, or may be obtained by collecting small-angle X-ray scattering information by radiation detection by detectors that are differently configured such as to be sensitive to different X-ray spectra. Thus, the first and second dark-field image may correspond to dark-field images obtained for different source spectra, or may be obtained from raw detector data acquired in accordance with different detector response functions (e.g. detector sensitivity as function of photon energy), or may correspond to a combination thereof (e.g. different radiation source spectra and collecting detector response functions). For example, the dark-field images may correspond to different energy channels of an energy-resolving detector, e.g. an energy-resolving photon counting detector, or to (substantially) different combinations of such energy channels.

As will be clearly understood by the skilled person, both first and second dark-field image represent the same region, e.g. chest region, of the same patient at substantially the same instant in time, e.g. in a single chest imaging examination, and are preferably naturally co-registered, e.g. obtained with substantially a same imaging geometry and at substantially the same moment in time (even though small and insignificant differences in imaging geometry and/or a small time interval between the image acquisitions for different spectra could obviously result from some system design choices, as would generally be understood in the art).

For example, the X-ray imaging apparatus 100 may be a dual energy imaging apparatus configured to image the patient (or at least the patient's thorax region) at two different (e.g. different mean or different peak) photon energies.

The X-ray imaging apparatus 100 may also be adapted to acquire more than two different images at corresponding different representative photon energies, e.g. may be spectral imaging apparatus that is capable of acquiring more than two different energy images. Thus, the input may be adapted for receiving image data that comprises more than two dark-field images obtained for respectively more than two different X-ray spectra.

The imaging apparatus is adapted for dark-field and/or phase contrast imaging. For example, the system may comprise a grating interferometer, e.g. comprise two or more gratings. For example, a three-grating interferometer arrangement may be used, as known in the art. This approach is particularly advantageous, since its implementation does not put any cumbersome constraints on the X-ray source 101 and detector 102, e.g. can be used, in principle, with a conventional X-ray source 101 and detector 102 as suitable for conventional attenuation X-ray imaging. For example, the imaging apparatus may be adapted for differential phase contrast imaging, e.g. using a Talbot-Lau-type interferometer. For example, the X-ray imaging apparatus 100 may comprise a source grating 103, generally positioned in use of the device between the X-ray source 101 and the object 106 to be imaged (e.g. the patient's chest), and a phase grating 104 and an absorption (or analyzer) grating 105, which are generally positioned in between the object 106 and the detector 102. The gratings may typically have well-defined grating line periods and may be positioned at well-defined distances with respect to each other, to the source and to the detector to obtain the desired effect, in accordance with established knowledge in the art. The source grating may create an array of individually coherent, yet mutually incoherent, virtual sources. However, it will be understood that alternatives exist for achieving the same or similar coherence of an X-ray beamlet. The phase grating may act so as to divide the beam into its first diffraction orders. The absorber grating may act as a transmission mask to transform local fringe variations into detectable intensity values, in which these fringe patterns may be created by the Talbot effect, e.g. particularly when the distance between the phase grating and the analyzer grating corresponds to the Talbot distance.

The X-ray imaging apparatus 100 may comprise a phase stepping mechanism to translate, e.g. in small steps, the phase grating with respect to the analyzer grating (or vice versa). This allows raw image detector data to be collected for each phase step, from which an X-ray attenuation image, a phase contrast image and a dark-field image can be reconstructed, using methods known in the art.

Dark-field imaging does not necessary require a phase stepping mechanism. For example, a fringe analysis method may be used, e.g. a spatial fringe scanning technique. Furthermore, the different dark-field images for different spectra are not necessarily acquired by using the same technique. For example, phase stepping may be used for one energy spectrum, and a spatial fringe scanning technique may be used for the other energy spectrum. Even though one of the images may have a lower spatial resolution, this may result in a reduced acquisition time. For example, the image acquired at the highest spatial resolution may be used to detect features of interest, e.g. abnormalities in the lungs, and the other image or images of lower spatial; resolution may be used to determine the type of abnormality, once detected.

The acquisition time may also be reduced by, instead of collecting the entire phase stepping curve (i.e. a fixed number of phase step points) for each spectrum separately, changing the spectrum (e.g. switching the source energy) while collecting the phase stepping curve. Thus, for example, two spectra (energies) may be alternated while going through the phase steps. It is also noted that the number of phase stepping sample points for each spectrum need not be equal. For example, a high number of phase steps may be determined for one spectrum, e.g. a reference spectrum, while only a few phase steps are used for another spectrum (and possibly further spectra). For example, the number of phase step samples needed to determine the dark-field signal may be less than the number of phase step samples needed to determine a phase-contrast signal. Thus, a reference spectrum may be used to obtain high-quality attenuation, phase-contrast and dark-field images, while a further spectrum (or further spectra) may be used to obtain only an additional dark-field image(s), which may have a lower spatial resolution or may be more noisy.

The device 1 may comprise a controller 7 for controlling the operation of the X-ray imaging apparatus 100, i.e. when the device is operably connected to the X-ray imaging apparatus, such as to acquire the image data. For example, the controller 7 may be adapted for controlling the X-ray source and/or the X-ray image detector. Furthermore, the controller 7 may be adapted for controlling the phase stepper mechanism of the X-ray imaging apparatus. For example, the controller 7 may be adapted for acquiring (raw) image data from the image detector for each of a plurality of phase steps, e.g. controlling the phase stepper mechanism to take a phase step before each image is acquired. As is known in the art, the dark-field image, as well as an attenuation image and phase contrast image, can be calculated from such raw image data collected for a plurality of phase steps. Hence, the device 1 may comprise a pixel value calculator to determine the dark-field signal value (and possibly also attenuation value and/or phase contrast value) for each image pixel from the raw image data (e.g. the different detected signal values corresponding to each of the phase steps). The controller 7 may be adapted for controlling the X-ray source such as to switch between the first X-ray spectrum for at least one (e.g. a first set) of the plurality of phase steps and the second X-ray spectrum for at least another (e.g. a second set) of the plurality of phase steps. For example, the controller may alternate between the two X-ray spectra while iterating over the phase steps.

However, other approaches to obtain phase contrast and/or dark-field image information (e.g. different grating interferometer designs or phase contrast/dark image imaging systems other than grating interferometer designs) are known in the art and are not necessarily excluded in embodiments of the present invention. Dark-field and contrast imaging systems are considered to be well-known in the art, and are therefore not discussed further in detail.

It is to be noted that, typically, contrast imaging information and dark-field imaging information can be obtained simultaneously by a same system, by specific, yet different, processing of the acquired raw image data. Likewise, attenuation image data can typically also be obtained from the same image data. However, for the purposes of the present application, the X-ray imaging apparatus 100 should be capable of generating dark-field image information, or raw data from which such dark-field image information can be derived. Nonetheless, it will be appreciated that phase contrast information and attenuation information may be obtained at (substantially) the same time, even though this is not strictly necessary, and may be presented as useful information to a user as well, e.g. to a clinician using the device in accordance with embodiments of the present invention. The dark-field image information, as known in the art, is generated by ultra-small angle scattering, e.g. multiple refractions on microstructures, whereas attenuation image contrast is caused by local differences in photon absorption and phase contrast is sensitive to electron density variations, e.g. may be caused by local variations in refractive properties (e.g. refractive index).

It will be appreciated that these three different and complementary image modalities, which can be advantageously obtained concomitantly, offer insight into different properties of the imaged object. The dark-field imaging component offers insight into structural properties of the imaged object, e.g. lung tissue, that arise at a scale that can be considerably smaller than the spatial resolution of the imaging system, i.e. smaller than the spatial detection threshold of the system.

The dark-field signal V (e.g. for a given geometric ray or pixel position) is a function of the so-called correlation length $??_{corr}$:

$V(??_{corr}) = \exp(??t(G(??_{corr})-1))$, in which is the sample thickness (as experienced by the ray at hand), and ?? is the total scattering probability per unit length, given by:

$$\sigma = \int \frac{d\sigma}{d\Omega}(Q_x) dQ_x.$$

Furthermore, the differential cross section can be expressed given by: as:

$$\frac{d\sigma}{d\Omega}(Q) = \left| \int_V \rho(r)\exp(iQr)dr \right|^2.$$

The correlation function can be calculated as $$G(x) = \frac{1}{\sigma} \int \frac{d\sigma}{d\Omega}(Q_x) \cdot \exp(iQ_x \cdot x) dQ_x,$$

and, typically, the correlation length may be calculated as: $\xi_{corr} = \lambda d_{G_2,s}/p_2$, where $\lambda$ is the wavelength, $p_2$ is the grating period of the absorption grating and $d_{G_2,s}$ is the distance between the sample and the absorption grating.

The grating period is typically predetermined and fixed. Furthermore, the distance between the sample and the absorption (analyzer) grating may also be preferably fixed, e.g. such as to maintain a constant magnification factor. However, a spectral imaging system, such as a dual-energy imaging apparatus (without limitation thereto), allows different wavelengths (or spectral components) of the X-ray beam to be detected independently. Therefore, the dark-field signal can (substantially) simultaneously (or at least concomitantly) be determined for different correlation lengths.

Figure 3:
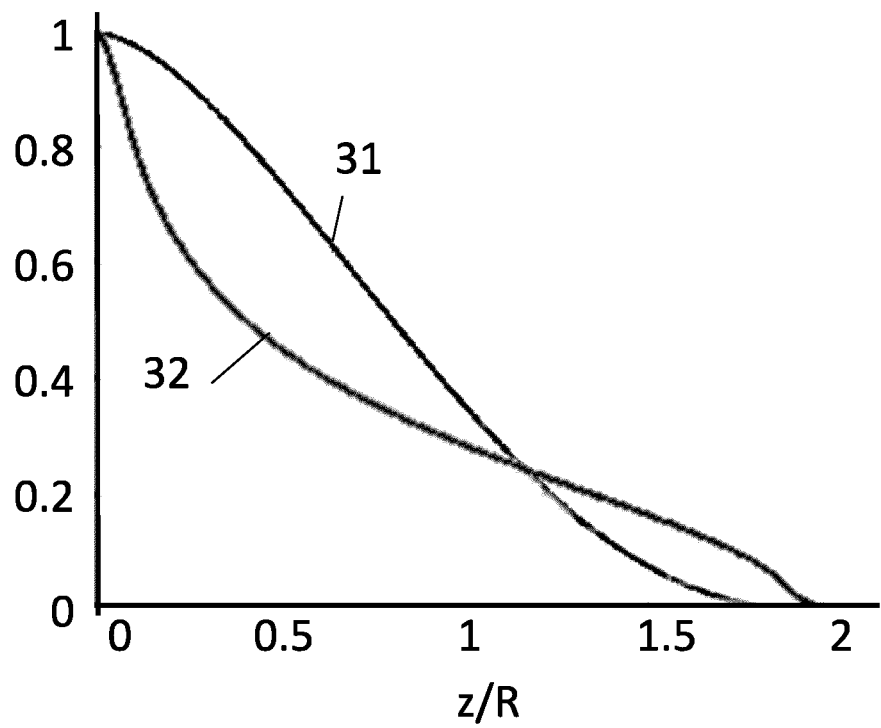
FIG. 3 illustrates correlation functions for different type of microstructure, to illustrate aspects of embodiments of the present invention.

If the X-ray radiographs are obtained at (at least) two different X-ray spectra, the dark-field signal changes for different correlation lengths, as implied by the different X-ray energies. Fitting a function to the measured dark-field signals yields additional information on the microstructure of the sample, i.e. complementary to the information on the microstructure that is already provided by the dark-field signal obtained at a single photon energy or for a single spectrum, e.g. such that the microstructure can be better characterized by this additional information. For example, the correlation function for a shell sphere (alveoli in a health state) and a solid sphere (fibrotic tissue, etc.) are very different and are shown below. FIG. 3 illustrates the correlation function G (z) for a sphere 31 and for a spherical shell 32. The x-axis has been normalized to units z/R of the sphere (and outer shell) radius R. In this example, the inner radius of the shell (plot line 32) corresponds to 0.9 times the outer radius R. As can be seen, certain conditions of the lung may correspond well (or better) with the solid sphere example, e.g. when scattering is caused by fluid-filled alveoli or fibrotic tissue, while other conditions of the lung may correspond well (or better) with the hollow shell example, e.g. healthy alveoli. However, it is noted that this is only an example to illustrate that different microstructures may correspond to substantially different correlation functions, and thus can be distinguished based on the dark-field images for different correlation lengths, i.e. different spectra, e.g. different energies.

The X-ray imaging apparatus 100 may comprise an X-ray source 101 and an X-ray detector 102. The X-ray source and/or the X-ray detector may be adapted for dual-energy and/or spectral imaging, i.e. to image the same object, e.g. the patient's thorax, at different representative photon energies and at substantially the same time (or acquisitions that are separated by a negligible fraction of time to obtain naturally aligned and registered images at different energies). For example, the X-ray source may be adapted to switch rapidly between at least two different photon spectra, e.g. by allowing the peak energy, kVp, to vary between different settings at a high switching rate. The different spectra may (alternatively or additionally) also be characterized by other features than only a different peak energy, e.g. different X-ray filtration, anode target properties, spot size, and/or the like. The X-ray detector may be adapted to switch between different response characteristics such as to be selectively sensitive to the different X-ray spectra, or may be adapted to acquire (raw) image data for different energy spectra simultaneously, e.g. by resolving multiple different energy windows for a same spatial point. For example, the X-ray detector may have different sensor elements that have (inherently or by a filter design) different sensitivities to the incident X-ray radiation, or may be able to determine the energy of incident photons directly. It is to be noted that a Dual-Energy or Spectral imaging apparatus can be achieved by specifically adapting the X-ray source 101, or the X-ray detector 102, or both the source and the detector, to be suitable for this purpose, as is known in the art. Dual-Energy and Spectral imaging systems are well-known in the art, and are therefore not described in full detail in the present description.

The X-ray imaging apparatus 100 may be a computed tomography system, e.g. may comprise a gantry to rotate the source, the detector, and further image formation elements, e.g. the interferometer gratings, around the object to be imaged, e.g. the patient. Such system may also comprise an image reconstructor, e.g. a processor or computer device adapted to reconstruct tomographic images from the image data acquired by the detector from a plurality of different projection angles, e.g. corresponding to different orientations of the gantry. However, the X-ray imaging apparatus 100 may also be digital projection radiography system, e.g. does not necessarily have tomographic reconstruction capabilities. For example, the X-ray imaging apparatus 100 may be adapted for acquiring the first and second dark-field image in a single projection view of the patient's thorax region, e.g. an anterior-posterior (AP) or posterior-anterior (PA) projection view image acquisition. Obviously, a user, e.g. a radiologist, may decide to capture multiple views from different angles, but the X-ray imaging apparatus 100 in accordance with embodiments of the present invention does not necessarily require the capabilities for executing a coordinated (e.g. automated) tomographic scan, e.g. a helical scan. Thus, the (first, second, further, . . . ) dark field images referred to in the present disclosure may refer to projection images, but may also refer to tomographic reconstructed images.

The device 1 comprises a combination unit 3 to calculate a combination image (e.g. a lung condition map) of the first dark-field image and the second dark-field image, e.g. such that a user can easily discern different pulmonary conditions when evaluating the combination image. For example, the combination image may show different pulmonary conditions differently, such as emphysema, COPD, and/or acute inflammation (without limitation).

The combination unit 3 may construct a vector-valued image from the first dark-field image and the second dark-field image, and optionally also (a) further dark-field image (s). For example, such vector-valued image may be a color image, in which different color components correspond to pixels in the different dark-field images. However, the vector values in this image can be constructed by a more intricate algorithm as well, e.g. showing an average of the dark-field images as a pixel intensity ('value') and a difference between the dark-field images as a color hue or as a color saturation, e.g. in a hue-saturation-value representation. If further images were obtained, different combinations can be contemplated to allow a visualization of the data. For example, a phase contrast or attenuation image may be used as one color component (e.g. 'value' or 'red'), while the dark-field images can be encoded in further color components (e.g. 'hue' and 'saturation' or 'green' and 'blue').

The combination unit 3 may be adapted to determine, for pixel locations in the combination image, a representation of the dark-field signal as function of photon energy (e.g. mean or peak energy) or as function of the correlation length. For example, while a limited number of dark-field images can be combined in a vector-valued image for visual evaluation, for a larger number of dark-field images, such combination may be less suitable, e.g. would require a selection of a limited number of features due to the constraints of human vision. However, the combination image may comprise such detailed functional representation, e.g. at least for pixels or regions of interest, such that a user can select a point in the image to view the corresponding function graph.

For example, the input 2 may be adapted for receiving the image data, in which the image data comprises a plurality of dark-field images (e.g. more than two, e.g. at least 4, e.g. at least 8, e.g. at least 16, e.g. at least 32, e.g. at least 64, e.g. at least 128, e.g. at least 256, . . . ) obtained for a corresponding plurality of (different) X-ray spectra. For example, the image data may be obtained from an energy-resolving detector, e.g. each image may comprise a dark-field component calculated on the basis of a different energy bin (or set of bins) as collected by the energy-resolving detector. Thus, the representation of the dark-field signal as function of energy may comprise a function specified by the dark-field values obtained for each of the energy bins, but may also comprise a parametric definition of a function determined from this data. For example, such parametric definition may comprise a spline representation, a Fourier representation, a linear, quadratic or cubic interpolation graph, a Gaussian mixture representation, or another suitable form. The combination unit may, for example, fit a parametric model to the data obtained for each pixel, and store the obtained parameters in the combination image.

The combination unit 3 may calculate a measure of deviation between the first dark-field image and the second dark-field image, and store this measure of deviation as pixel values (or components of the pixel values) in the combination image. For example, such measure of deviation may be a difference, an absolute difference, a ratio, and logarithm of a difference, and/or another suitable operation for comparing two values (in absolute or relative terms). It can be seen that a ratio might be a useful measure, e.g. of a dark-field signal obtained for a relatively low photon energy (e.g. longer wavelength, longer correlation length) divided by a dark-field signal (for a corresponding pixel location) obtained for a relatively high photon energy (e.g. shorter wavelength, shorter correlation length). Such ratio may be used as an approximation or alternative to the slope of the correlation function, which could encode useful information regarding the nature of an underlying condition (see e.g. the substantially different slopes near, for example, z/R=0 in FIG. 3).

The combination image may be suitable for presentation to a user, e.g. a radiologist, but may also be a technical image for use in further image processing, such as image segmentation.

The device 1 may also comprise a segmenter 4 for segmenting an image to identify lung structures of interest, e.g. regions afflicted by an abnormal pulmonary condition. The image used by this segmenter may be one of the dark-field images, the combination image, or another image received via the input, e.g. an attenuation image or phase contrast image. The segmenter may also use different images, e.g. in a stepwise segmentation approach or as vector-valued compound image. For example, X-ray attenuation information may be used to determine a lung mask image, e.g. as mask to limit a further segmentation of different lung structures of interest, e.g. based on the combination image.

Referring to US 2018/271465, the device may also comprise a normalization unit be adapted for normalizing the first dark-field image, the second dark-field image and/or any further dark-field image, by using a lung depth map for normalization. Such lung depth map can be calculated, as described in detail in the aforementioned patent application, by applying a bone suppression algorithm (which can be, advantageously, performed based on spectral attenuation information, e.g. which may already be available in the same raw detector data that was acquired to calculate the first dark field image and the second dark field image) and applying a radiation attenuation model to the boneless lung image data.

The device 1 may also comprise a classifier 5 for labelling segmented lung structures with a plurality of classifier labels based on the combination image. The classifier labels correspond to different pulmonary conditions, e.g. (two or more selected from:) inflamed lung tissue, emphysema, lung cancer nodule, COPD, cystic fibrosis, bronchiectasis, pleural effusion, etc. The classifier may be adapted for annotating the combination image with the labeled segmented lung structures to obtain an annotated image.

Thus, the classifier 5 may select, for each detected lung structure, one of a plurality of possible labels, based on the combination image. However, the classifier 5 may also take other image information into account, such as one or more (e.g. for different spectra) attenuation images, one or more (e.g. for different spectra) phase contrast images, or even images obtained by different modalities (e.g. preferably co-registered to the other images used).

The device 1 may comprise an output 6 for outputting the combination image and/or the segmented image and/or the annotated image. The output may comprise a data storage device, a network connection, a data bus or another type of digital communication and/or storage interface. The output may also comprise a user interface device, such as a computer monitor, a printer, and the like, to display the combination image. Such user interface may also comprise means for receiving (e.g. interactive) commands from a user, as known in the art. Thus, the combination image may be presented to a user, e.g. a radiologist, of review. It is an advantage that by combining dark-field images for different X-ray energies (different spectra), the user can distinguish between different lung conditions more easily without requiring additional imaging (e.g. further examination using different imaging modalities) or further examination (e.g. functional lung tests, biopsy, etc.).

In a third aspect, the present invention relates to a clinical workstation comprising an image processing device 1 as described hereinabove. The clinical workstation may be adapted for presenting visual information, e.g. an imaging visualization workstation. The workstation may comprise one or more graphical display devices, e.g. monitors, a user interface device(s), such as a keyboard and/or a mouse and/or other human interface devices known in the art, and a processor. The workstation may be embodied by a computer, a smartphone, a tablet, a network server computer, and/or combinations thereof. Such clinical workstation may be suitable for or integrated in a radiology suite, a biopsy lab suite, an operating theatre suite, a radiotherapy planning and/or execution system, and the like.

Figure 4:
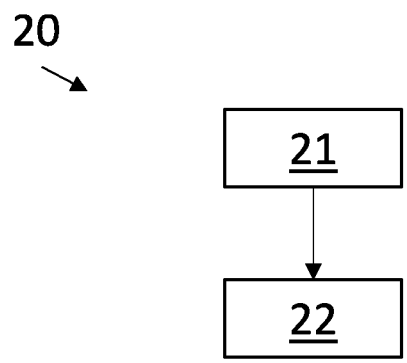
FIG. 4 shows a method in accordance with embodiments of the present invention.

Referring to FIG. 4, in a fourth aspect, the present invention relates to a method 20, e.g. a computer-implemented method, for processing image data. The method 20 comprises obtaining 21 image data representative of a patient's region of interest from a medical X-ray imaging apparatus. The image data comprises a first dark-field image obtained for a first X-ray spectrum and a second dark-field image obtained for a second X-ray spectrum, wherein said first X-ray spectrum and said second X-ray spectrum are substantially different. The method comprises providing 22 a combination image that is representative of a lung condition map by combining the first dark-field image and the second dark-field image.

Other features, or details of the features described hereinabove, of a method in accordance with embodiments of the present invention shall be clear in view of the description provided hereinabove relating to a device and/or system in accordance with embodiments of the present invention.

In a fifth aspect, the present invention relates to a computer program product for performing a (e.g. computer-implemented) method in accordance with embodiments of the present invention when executing the computer program product on a suitable processor.

In a sixth aspect, the present invention relates to a medical diagnostic image of a chest region of a patient, comprising a combination of a first dark-field image obtained for a first X-ray spectrum and a second dark-field image obtained for a second X-ray spectrum, wherein the first X-ray spectrum and the second X-ray spectrum are different.

The invention claimed is:

1. An image processing device, comprising:
    an input for receiving image data representative of a region of interest in a body of a patient, wherein the image data comprises a first dark-field image obtained for a first X-ray spectrum and a second dark-field image obtained for a second X-ray spectrum, wherein the first X-ray spectrum and the second X-ray spectrum are different; and
    a processor configured to provide a combination image that is representative of a condition map by combining the first dark-field image and the second dark-field image.

2. The image processing device of claim 1, wherein the region of interest is a thorax region, and wherein the condition map is a lung condition map.

3. The image processing device of claim 1, wherein the processor is adapted for constructing the combination image as a vector-valued image, the vector-valued image having components that correspond to, or are calculated on the basis of, the first dark-field image and the second dark-field image.

4. The image processing device of claim 1, wherein the processor is adapted to determine, for pixel locations in the combination image, a dark-field signal as function of photon energy or as function of correlation length.

5. The image processing device of claim 1, wherein the processor is adapted to calculate a measure of deviation between the first dark-field image and the second dark-field image, wherein pixel values in the combination image correspond to the measure of deviation.

6. The image processing device of claim 1, furthermore comprising a controller for controlling acquisition of the image data.

7. The image processing device of claim 6, wherein the controller is adapted for stepping through a plurality of phase steps by controlling a phase stepper, acquiring image data from an image detector for each of a plurality of phase steps, and for controlling an X-ray source such as to switch between the first X-ray spectrum for at least one of the plurality of phase steps and the second X-ray spectrum for at least another of the plurality of phase steps.

8. The image processing device of claim 1, comprising a segmenter for segmenting the first dark-field image, the second dark-field image, the combination image, or another image received via the input in order to identify structures of interest.

9. The image processing device of claim 8, comprising a classifier for labelling each identified structure of interest with a classifier label that is selected by the classifier from a plurality of classifier labels based on the combination image, the plurality of classifier labels corresponding to different conditions.

10. A computer-implemented method for processing image data, comprising:
    obtaining image data representative of a region of interest in a body of a patient, wherein the image data comprises a first dark-field image obtained for a first X-ray spectrum and a second dark-field image obtained for a second X-ray spectrum, wherein the first X-ray spectrum and the second X-ray spectrum are different; and
    generating a combination image that is representative of a condition map by combining the first dark-field image and the second dark-field image.

11. The method of claim 10, wherein the region of interest is a thorax region, and wherein the condition map is a lung condition map.

\* \* \* \* \*